US007815852B2

(12) United States Patent
Sternby

(10) Patent No.: US 7,815,852 B2
(45) Date of Patent: Oct. 19, 2010

(54) METHOD, APPARATUS AND SOFTWARE PROGRAM FOR MEASUREMENT OF A PARAMETER RELATING TO A HEART-LUNG SYSTEM OF A MAMMAL

(75) Inventor: Jan Peter Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 1194 days.

(21) Appl. No.: 10/990,967

(22) Filed: Nov. 18, 2004

(65) Prior Publication Data
US 2005/0148923 A1 Jul. 7, 2005

Related U.S. Application Data

(60) Provisional application No. 60/524,190, filed on Nov. 20, 2003.

(51) Int. Cl.
A61M 1/00 (2006.01)
A61M 37/00 (2006.01)
A61M 5/05 (2006.01)
A61B 5/00 (2006.01)
A61B 8/00 (2006.01)
A61B 5/04 (2006.01)
B01D 63/00 (2006.01)
C02F 1/44 (2006.01)

(52) U.S. Cl. .................. 422/44; 604/4.01; 604/5.01; 604/6.09; 604/6.11; 600/309; 600/310; 600/316; 600/322; 600/345; 600/365; 600/437; 600/481; 600/504; 210/321.71

(58) Field of Classification Search .................. None
See application file for complete search history.

(56) References Cited

U.S. PATENT DOCUMENTS 2,709,785 A   5/1955   Fielden
3,304,413 A * 2/1967   Lehmann et al. .............. 377/19
3,324,720 A   6/1967   Sutherland (Continued)

FOREIGN PATENT DOCUMENTS

DE   4024434   2/1992

(Continued)

OTHER PUBLICATIONS

Online Encyclopedia. http://en.wikipedia.org/wiki/Blood_urea_nitrogen.*

(Continued)

Primary Examiner—Tatyana Zalukaeva
Assistant Examiner—Adam Marcetich
(74) Attorney, Agent, or Firm—Finnegan, Henderson, Farabow, Garrett & Dunner, L.L.P.

(57) ABSTRACT

A method, apparatus and software program for measuring a parameter relating to the heart-lung system of a mammal are described. The method, software and apparatus can be implemented in a dialysis or other blood treatment apparatus comprising an extracorporeal blood circuit connected to a mammal; the circuit comprises a dialyzer, or other treatment unit, having a blood inlet, a blood outlet, a treatment fluid inlet and a treatment fluid outlet. The method comprises the steps of providing a pulse of a detectable substance in the blood circuit, measuring an integrated concentration of the detectable substance on the dialysis fluid outlet, determining the parameter based on the measurements on the dialysis fluid outlet.

28 Claims, 3 Drawing Sheets

U.S. PATENT DOCUMENTS

| | | |
|---|---|---|
| 3,396,331 A | 8/1968 | Sperry, III |
| 3,404,336 A | 10/1968 | Rosenthal |
| 3,433,935 A | 3/1969 | Sherman |
| 3,446,073 A | 5/1969 | Auphan et al. |
| 3,450,984 A | 6/1969 | Holmes |
| 3,482,575 A | 12/1969 | Ciaff et al. |
| 3,491,592 A | 1/1970 | Evers et al. |
| 3,545,428 A | 12/1970 | Webster, Jr. |
| 3,561,266 A | 2/1971 | Auphan et al. |
| 3,604,263 A | 9/1971 | Auphan et al. |
| 3,619,423 A | 11/1971 | Galletti et al. |
| 3,640,271 A | 2/1972 | Horton |
| 3,722,276 A | 3/1973 | Chandler et al. |
| 3,733,899 A | 5/1973 | Auphan et al. |
| 3,867,688 A | 2/1975 | Koski |
| 3,964,479 A | 6/1976 | Boag et al. |
| 3,980,946 A | 9/1976 | Fleury |
| 3,985,134 A | 10/1976 | Lissot et al. |
| 3,987,788 A | 10/1976 | Emil |
| 4,081,372 A | 3/1978 | Atkin et al. |
| 4,136,563 A | 1/1979 | Mueller et al. |
| 4,138,639 A | 2/1979 | Hutchins |
| 4,153,418 A | 5/1979 | Haas |
| 4,167,870 A | 9/1979 | Haas |
| 4,181,610 A | 1/1980 | Shintani et al. |
| 4,361,049 A | 11/1982 | Volgyesi |
| 4,391,124 A | 7/1983 | Drost et al. |
| 4,432,231 A | 2/1984 | Napp et al. |
| 4,434,648 A | 3/1984 | Drost et al. |
| 4,446,871 A | 5/1984 | Imura |
| 4,508,622 A | 4/1985 | Polaschegg et al. |
| 4,650,458 A | 3/1987 | Dahlberg et al. |
| 4,715,849 A | 12/1987 | Gion et al. |
| 4,739,492 A | 4/1988 | Cochran |
| 4,740,755 A | 4/1988 | Ogawa |
| 4,777,958 A | 10/1988 | Ophir |
| 4,797,655 A | 1/1989 | Orndal et al. |
| 4,822,341 A | 4/1989 | Colone |
| 4,825,168 A | 4/1989 | Ogawa et al. |
| 4,856,321 A | 8/1989 | Smalling et al. |
| 4,885,001 A | 12/1989 | Leppert |
| 4,885,087 A | 12/1989 | Kopf |
| 4,923,598 A | 5/1990 | Schäl |
| 4,995,268 A | 2/1991 | Ash et al. |
| 5,004,459 A | 4/1991 | Peabody et al. |
| 5,024,756 A | 6/1991 | Sternby |
| 5,058,416 A | 10/1991 | Engelhardt et al. |
| 5,092,836 A | 3/1992 | Polaschegg |
| 5,098,373 A | 3/1992 | Polaschegg |
| 5,100,554 A | 3/1992 | Polaschegg |
| 5,230,341 A | 7/1993 | Polaschegg |
| 5,312,550 A | 5/1994 | Hester |
| 5,357,967 A | 10/1994 | Dixon et al. |
| 5,372,136 A | 12/1994 | Steuer et al. |
| 5,442,969 A | 8/1995 | Troutner et al. |
| 5,453,576 A | 9/1995 | Krivitski |
| 5,507,723 A | 4/1996 | Keshaviah |
| 5,510,716 A | 4/1996 | Buffaloe, IV et al. |
| 5,510,717 A | 4/1996 | Buffaloe, IV et al. |
| 5,518,623 A | 5/1996 | Keshaviah et al. |
| 5,567,320 A | 10/1996 | Goux et al. |
| 5,570,026 A | 10/1996 | Buffaloe, IV et al. |
| 5,588,959 A | 12/1996 | Ahmad et al. |
| 5,595,182 A | 1/1997 | Krivitski |
| 5,605,630 A | 2/1997 | Shibata |
| 5,644,240 A | 7/1997 | Brugger |
| 5,662,806 A | 9/1997 | Keshaviah et al. |
| 5,685,988 A | 11/1997 | Malchesky |
| 5,685,989 A | 11/1997 | Krivitski et al. |
| 5,830,365 A * | 11/1998 | Schneditz .................. 210/739 |
| 5,866,015 A | 2/1999 | Krämer |
| 5,894,011 A | 4/1999 | Prosl et al. |
| 5,900,726 A | 5/1999 | Brugger et al. |
| 5,902,253 A | 5/1999 | Pfeiffer et al. |
| 6,061,590 A | 5/2000 | Krivitski |
| 6,090,048 A | 7/2000 | Hertz et al. |
| 6,110,384 A * | 8/2000 | Goux et al. .................. 210/739 |
| 6,117,099 A | 9/2000 | Steuer et al. |
| 6,153,109 A | 11/2000 | Krivitski |
| 6,177,049 B1 | 1/2001 | Schnell et al. |
| 6,189,388 B1 | 2/2001 | Cole et al. |
| 6,210,591 B1 | 4/2001 | Krivitski |
| 6,221,040 B1 | 4/2001 | Kleinekofort |
| 6,308,737 B1 | 10/2001 | Krivitski |
| 6,623,443 B1 | 9/2003 | Polaschegg |
| 6,691,040 B2 | 2/2004 | Bosetto et al. |
| 2001/0031222 A1 | 10/2001 | Schnell et al. |
| 2001/0050256 A1 | 12/2001 | Krivitski |
| 2003/0060722 A1 * | 3/2003 | Pfeiffer et al. ............... 600/504 |

FOREIGN PATENT DOCUMENTS

| | | |
|---|---|---|
| DE | 19537688 | 5/1996 |
| DE | 19528907 | 11/1996 |
| DE | 19541783 | 3/1997 |
| DE | 19901078 | 2/2000 |
| EP | 0018817 | 11/1980 |
| EP | 0089003 | 9/1983 |
| EP | 0097366 | 1/1984 |
| EP | 0272414 | 6/1988 |
| EP | 0590810 | 4/1994 |
| EP | 0 658 352 | 6/1995 |
| EP | 0693296 | 1/1996 |
| EP | 0693297 | 1/1996 |
| EP | 0773035 | 5/1997 |
| EP | 0835669 | 4/1998 |
| EP | 0845273 | 6/1998 |
| EP | 0900094 | 3/1999 |
| EP | 0911043 | 4/1999 |
| EP | 0 920 877 | 6/1999 |
| EP | 0928614 | 7/1999 |
| EP | 0943369 | 9/1999 |
| EP | 1044695 | 10/2000 |
| EP | 1083947 | 3/2001 |
| EP | 1 108 438 | 6/2001 |
| EP | 1106191 | 6/2001 |
| ES | 2026508 T | 5/1992 |
| GB | 2093192 | 8/1982 |
| JP | 60190873 | 9/1985 |
| JP | 5236990 | 9/1993 |
| SU | 521891 | 10/1976 |
| SU | 1013853 | 5/1981 |
| WO | WO-96/08305 | 3/1996 |
| WO | WO-97/01289 | 1/1997 |
| WO | WO-97/10013 | 3/1997 |
| WO | WO-98/17193 | 4/1998 |
| WO | WO-98/17334 | 4/1998 |
| WO | WO-98/32477 | 7/1998 |
| WO | WO-99/64088 | 12/1999 |
| WO | WO-00/18451 | 4/2000 |
| WO | WO-00/24440 | 5/2000 |
| WO | WO-00/74732 | 12/2000 |
| WO | WO-01/08719 | 2/2001 |
| WO | WO-02/04044 | 1/2002 |

OTHER PUBLICATIONS

F. M. De Freitas, E. Z. Faraco, N. Nedel, D. F. De Azevedo and J. Zaduchliver. Determination of Pulmonary Blood Volume by Single Intravenous Injection of One Indicator in Patients with Normal and High Pulmonary Vascular Pressures. Circulation 1964;30;370-380. Print ISSN: 0009-7322. Online ISSN: 1524-4539.*

Hester et al., "A New Technique for Determining Recirculation in the ESRD Patient," *Nephrology News & Issues*, pp. 44-45 (Jun. 1993).

Petitclerc et al., "A model for non-invasive estimation of in vivo dialyzer performances and patient's conductivity during hemodialysis," *The International Journal of Artificial Organs*, vol. 16, No. 8, pp. 585-591 (1993).

Petitclerc et al., "Non-invasive monitoring of effective dialysis dose delivered to the hemodialysis patient," *Nephrology Dialysis Transplantation*, 10: 212-216 (1995).

Mercadal et al., "Determination of access blood flow from ionic dialysance: Theory and validation," *Kidney International*, vol. 56, pp. 1560-1565 (1999).

Gambro Ltd., "FAM 10, Fistula Flow Studies and Their Interpretation," pp. 1-31, published on or before Sep. 29, 1991.

Salamon et al., "A Low Frequency Electrodeless Conductometer for Measuring the Electrical Conductivity of Solutions," *Industrial Group Headquarters*, pp. 3-12 (1959).

Sherman, "Recirculation Revisited," *Seminars in Dialysis*, vol. 4, No. 4, pp. 221-223 (Oct.-Dec. 1991).

Smith et al., "Cardiac Output Determined by the Saline Conductivity Method Using an Extraarterial Conductivity Cell," *Cardiovascular Research Center Bulletin*, vol. 5, No. 4, pp. 123-134 (1967).

Thomsen et al., "Evaluation of Clinical Examination Preceding Surgical Treatment of Av-Fistula Problems," *Acta Chir Scand*, vol. 151, pp. 133-137 (1985).

Transonic Systems Inc., "Access Flow & Recirculation Measured During Hemodialysis," (Oct. 1994).

Aldridge et al., "The assessment of arteriovenous fistulae created for hemodialysis from pressure and thermal dilution measurements," *Journal of Medical Engineering Technology*, vol. 8, No. 3, pp. 118-124 (May-Jun. 1984).

Aldridge et al., "Instrument Design for the Bedside Assessment of Arteriovenous Fistulae in Haemodialysis Patients," *Proc EDTNA-ERCA*, vol. 14, pp. 255-260 (1985).

Carr, Integration of Decaying Exponential Sensor Output Signals, *Sensors*, pp. 28-34 (Jul. 1989).

Daugirdas et al., "The Fourth Annual Advanced Dialysis Technical Symposium, Jun. 10, 1988," *Dialysis & Transplantation*, vol. 17, No. 8, pp. 432-433 (Aug. 1998).

Fresenius Dialysetechnik "BTM 4008 Fistelrezirkulation," (Nov. 1993).

Gambro "Fistula Assessment Monitor FAM 10," (aprx. 1985).

Gambro "Fistula Assessment Monitor FAM 10 Operator's Manual," (aprx. 1985).

Gambro "Fistula Assessment Monitor FAM 10 Service Manual," (aprx. 1985).

Gani et al., "Use of the Fistula Assessment Monitor to Detect Stenoses in Access Fistulae," *American Journal of Kidney Diseases*, vol. XVII, No. 3, pp. 303-306 (Mar. 1991).

Greenwood et al., "Assessment of Arteriovenous Fistulas from Pressure and Recirculation Studies: Clinical Experience in 215 Upper Limb Fistulas," *Proc EDRA-ERA*, vol. 22, pp. 296-302 (1985).

Greenwood et al., "Assessment of Arteriovenous Fistulae from Pressure and Thermal Dilution Studies: Clinical Experience in Forearm Fistulae, " *Clinical Nephrology*, vol. 23, No. 4, pp. 189-197 (1985).

Goldstein et al., "The Assessment of Arteriovenous Fistulae from Pressure and Recirculation Studies," *Proc EDTNA-ERCA*, vol. 14, pp. 207-215 (1985).

Hart et al., "A Noninvasive Electromagnetic Conductivity Sensor for Biomedical Applications," *IEEE Transactions on Biomedical Engineering*, vol. 35, No. 12, pp. 1011-1019 (Dec. 1988).

Hester et al., "The Determination of Hemodialysis Blood Recirculation Using Blood Urea Nitrogen Measurements," *American Journal of Kidney Diseases*, vol. XX, No. 6, pp. 598-602 (Dec. 1992).

Kramer et al., "Automated Measurement of Recirculation," *EDTNA-ERCA Journal*, vol. XIX, No. 2, pp. 6-9 (Apr. 1993).

Kramer et al., "A Device for Control of Thermal Parameters and Recirculation Measurement in Hemodialysis," *Fourth Annual British Renal Symposium*, Abstract (Nov. 1992).

"Transonic® Hemodialysis Monitor Measures Access Flow Recirculation Cardiac Output Routinely During Dialysis," *EDTA-ERCA* (Apr. 1995).

Depner et al., Clinical Measurement of Blood Flow in Hemodialysis Access Fistulae and Grafts by Ultrasound Dilution, *ASAIO Journal*, pp. M745-749 (Jul. 1995).

Depner et al., "Hemodialysis Access Recirculation Measured by Ultrasound Dilution," *Asaio Journal*, pp. M749-M753 (Jul. 1995).

Krivitski, "Novel Method to Measure Access Flow During Hemodialysis by Ultrasound Velocity Dilution Technique," *ASAIO Journal*, pp. M741-745 (1995).

Krivitski, "Theory and Validation of Access Flow Measurement by Dilution Technique During Hemodialysis," *Kidney International*, vol. 48, pp. 244-250 (1995).

Krivitski, "Accuracy of Ultrasound Dilution Method to Measure Access Flow (AF) in Hemodialysis," *XIIIth International Congress of Nephrology*, Abstract (1995).

Krivitsky, "New Method to Measure Recirculation (Rc) and Access Flow During Hemodialysis (HD)," *American Nephrology Nurses' Association 26th National Symposium Exhibitor Continuing Education Program*, Abstract (1995).

Depner, "Changes in Access Blood Flow (Qac) and Appearance of Recirculation (RC) During Hemodialysis," *XIIIth International Congress of Nephrology*, Abstract (1995).

Depner et al., "Hemodialysis Access Recirculation (Rc) Measured by Ultrasound Dilution," *ASAIO Journal*, Abstract, vol. 41, No. 1, p. 80 (1995).

Depner et al., "Clinical Measurement of Blood Flow in Hemodialysis Access Fistulae and Grafts by Ultrasound Dilution," *ASAIO Journal*, Abstract, vol. 41, No. 1, p. 80 (1995).

Transonic Systems Inc., "Recirculation, Access Flow Measurements, The Hemodialysis Monitor," pp. 19-26 1995).

Krivitski, "Cardiac Output Measurement in Extracorporeal Systems by Ultrasound Velocity Dilution," *ASAIO Journal*, American Society of Internal Organs, 40th Anniversary Meeting, 1994 Abstracts, Abstract, p. 82 (1995).

Sands et al., The Effect of Doppler Flow Screening Studies and Elective Revisions on Dialysis Access Failure, *ASAIO Transactions*, pp. M524-M527 (1992).

Nosher, "Death, Taxes, and Vascular Access Dysfunction," *Seminars in Dialysis*, vol. 4, No. 2, pp. 67-28 (1991).

In-Line Diagnostics, "Improve the Clinical Outcome of Every Patient with Crit-Line," Brochure, four pages (undated).

In-Line Diagnostics, "Noninvasive Blood Volume Monitoring, Blood Volume Profile," Brochure, two pages (1994).

In-Line Diagnostics, "The Crit-Line System," Brochure, two pages (undated).

Bower et al., "Circulatory Function During Chronic Hemodialysis," *Amer. Soc. Artif. Int. Organs*, vol. XV, pp. 373-377 (1969).

Aldridge et al., "The Use and Management of Arteriovenous Fistulae Fact and Fiction," *EDTNA-ERCA Journal*, vol. XVII-4, pp. 29-35 (1991).

Hester et al., "Non-invasive Determination of Recirculation in the Patient on Dialysis," *ASAIO Journal*, pp. M190-M193 (1992).

Hester et al., "Non-invasive Measurement of Recirculation in the Dialysis Patient," Abstract No. 7 (1992).

Greenwood et al., "Single Needle Dialysis," *Journal of Medical Engineering & Technology*, vol. 6, No. 3, pp. 93-98 (1982).

Konner et al., "Transvenous Serial Xero-Arteriography: A New Noninvasive Angiographic Method for AV-Fistulas in Haemodialysis Patients," *Proc EDTA*, vol. 18, pp. 305-309 (1981).

Forsberg et al., "Quantitative Doppler and Ultrasound Measurements in Surgically Performed Arteriovenous Fistulas of the Arm," *Acta Radiologica Diagnosis 21*, Fasc. 6, pp. 769-771 (1980).

Schneditz et al., "Cardiopulmonary Recirculation in Dialysis," *ASAIO Journal*, M194-M196 (1992).

Guyton, "The Indicator Dilution Method," *Text Book of Medical Physiology*, pp. 287-288 (1991).

Gothlin et al., "A Dye-dilution Method for the Determination of Blood Flow in Cimino-brescia Arteriovenous Fistulae," *Investigative Urology*, vol. 15, No. 2, pp. 167-168 (1977).

Oudenhoven et al., "Magnetic Resonance, A New Method for Measuring Blood Flow in Hemodialysis Fistulae," *Kidney International*, vol. 45, pp. 884-889 (1994).

Rocha et al., "Arteriovenous Shunt Measured by Bolus Dye Dilution: Reproducibility and Comparison Between Two Injection Sites," *Catheterization and Cardiovascular Diagnosis*, vol. 11, pp. 473-481 (1985).

Gottlieb et al., "Radiotracer Method for Nonsurgical Measurement of Blood Flow in Bovine Graft Arteriovenous Fistulas," *Proc. Dialysis Transplant Forum*, pp. 107-108 (1976).

Lantz et al., "Determination of Blood Flow Through Arteriovenous Fistulae and Shunts," *Acta Radiologica Diagnosis* 20, vol. 5, pp. 727-736 (1979).

Depner et al., "Access Flow Measured From Recirculation of Urea During Hemodialysis with Reversed Blood Lines," *JASN*, Abstract, vol. 6, p. 486 (1995).

Lindsay et al., "Monitoring Vascular Access Flow," *Advances in Renal Replacement Therapy*, vol. 6, No. 3, pp. 273-277 (1999).

Lindsay et al., "Estimation of Hemodialysis Access Blood Flow Rates by a Urea Method Is a Poor Predictor of Access Outcome," *ASAIO Journal*, vol. 44, pp. 818-822 (1988).

Sternby, "Urea Sensors-A World of Possibilities," *Advances in Renal Replacement Therapy*, vol. 6, No. 3, pp. 265-272 (1999).

Yarar et al., "Ultrafiltration Method for Measuring Vascular Access Flow Rates During Hemodialysis," *Kidney International*, vol. 56, pp. 1129-1135 (1999).

Polaschegg et al., On-line Dynamic Measurement of Fistula Pressure During Haemodialysis for Detection of Access Stenosis and Bad Needle Placement, *XXVIth Conference EDTNA-ERCA*, Abstract, p. 23 (1997).

Polaschegg et al., "Dynamic Pressure Measurement for Detection of Blood Access Stenosis," *EDTNA-ERCA Journal*, vol. XXIV, No. 4, pp. 39-44 (1998).

Polaschegg, "Pressure Drops in Cannulas for Hemodialysis," *The International Journal of Artificial Organs*, vol. 24, No. 9, pp. 614-623 (2001).

Lodi et al., "A Novel Model-based Method for Monitoring the Hemodialysis Vascular Access," *ASN/ISN Congress*, Abstract, pp. 294A-295A (2001).

Frinak et al., Dynamic Venous Access Pressure Ratio Test for Hemodialysis Access Monitoring, *American Journal of Kidney Diseases*, vol. 40, No. 4, pp. 760-768 (2002).

Besarab et al., "Utility of Intra-access pressure Monitoring in Detecting and Correcting Venous Outlet Stenoses Prior to Thrombosis," *Kidney International*, vol. 47, pp. 1364-1373 (1995).

Besarab et al., "Effects of Systemic Hemodynamics on Flow Within Vascular Accesses Used for Hemodialysis," *ASAIO Journal*, vol. 47, pp. 501-506 (2001).

Kleinekofort et al., "Extracorporeal Pressure Monitoring and the Detection of Vascular Access Stenosis," *The International Journal of Artificial Organs*, vol. 25, No. 1, pp. 45-50 (2002).

Besarab et al., "Detection of Access Strictures and Outlet Stenoses in Vascular Accesses," *ASAIO Journal*, vol. 43, pp. M543-M547 (1997).

Besarab et al., "Simplified Measurement of Intra-access Pressure," *Journal of the American Society of Nephrology*, vol. 9, pp. 284-289 (1997).

International Search Report for International Application No. PCT/SE99/01915.

Paul G. Sakiewicz, et al., "Introduction of a Switch that Can Reverse Blood Flow Direction On-Line during Hemodialysis" *ASAIO Journal*, vol. 46, n.4, Jul. 2000, pp. 464-468.

International Search Report for International Application No. PCT/IB2004/003635.

* cited by examiner

FIG 1
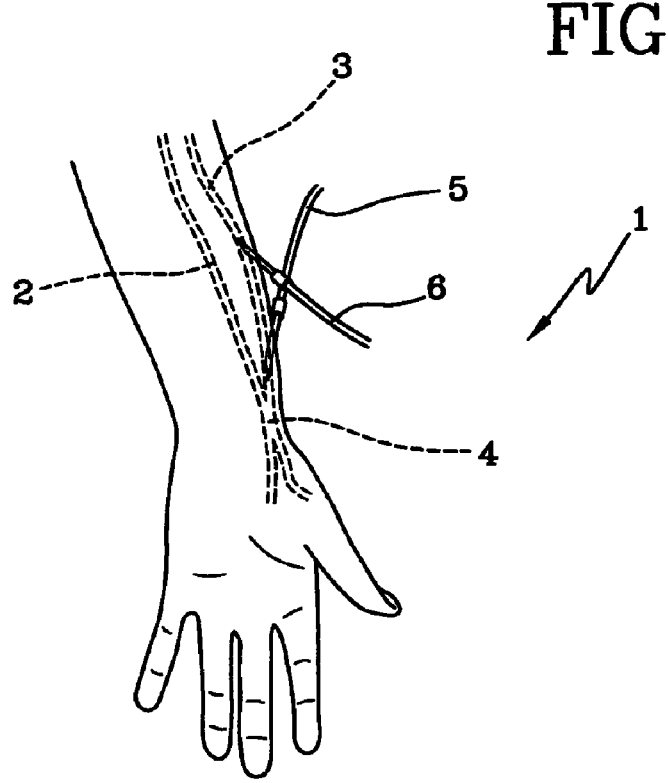
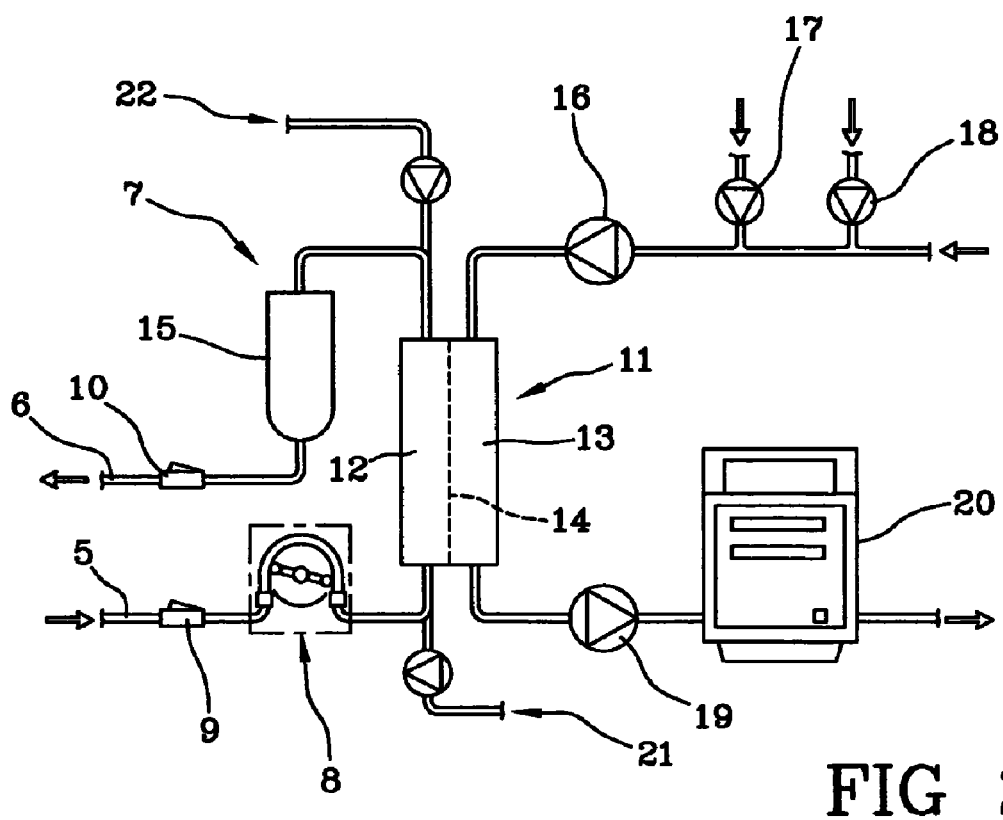
FIG 2

METHOD, APPARATUS AND SOFTWARE PROGRAM FOR MEASUREMENT OF A PARAMETER RELATING TO A HEART-LUNG SYSTEM OF A MAMMAL

CROSS REFERENCE TO RELATED APPLICATIONS

This application claims the benefit of U.S. Provisional Application No. 60/524,190, filed on Nov. 20, 2003, the contents of which are incorporated herein by reference.

TECHNICAL FIELD

The present invention relates to a method, apparatus and software program for measuring a parameter relating to the heart-lung system of a mammal. Parameters relating to the heart-lung system of a mammal are the cardiac output, the heart-lung volume or other parameters proportional to the cardiac output and/or to the heart-lung volume.

The method, apparatus and software program of the invention can be used for instance for measuring the cardiac output and/or the heart-lung volume when a mammal is connected to a blood treatment equipment.

PRIOR ART

There are several types of treatments in which blood is taken out of a live body in an extracorporeal blood circuit. Such treatments involve, for example, hemodialysis, hemofiltration, hemodiafiltration, plasmapheresis, blood component separation, blood oxygenation, etc. Normally, blood is removed from a blood vessel at a blood access and returned to another or to the same blood vessel.

In hemodialysis and similar treatments, a blood access is commonly surgically created in the nature of an arteriovenous shunt, commonly referred to as a fistula. Blood needles are inserted into the fistula. Blood is taken out from the fistula via a needle at an upstream position and blood is returned to the fistula via a needle at a downstream position.

The arterio-venous shunt or fistula is a blood access having capability of providing a high blood flow rate and being operative during several years and, in some instances perhaps even tens of years. It is produced by operatively connecting, for example, the radial artery to the cephalic vein at the level of the forearm. The venous limb of the fistula thickens during the course of several months, permitting repeated insertion of dialysis needles.

An alternative blood access to the fistula is the arteriovenous graft, in which a connection is generated from, for example, the radial artery at the wrist to the basilic vein. The connection is made with a tube graft made from e.g. autogenous saphenous vein or from polytetrafluoroethylene (PTFE, Teflon). The needles are inserted into the graft.

A further example of a blood access is a dual-lumen catheter surgically implanted into one of the large veins.

Further types of blood access find use in specific situations, like a no-needle arterio-venous graft consisting of a T-tube linked to a standard PTFE graft. The T-tube may be implanted in the skin. Vascular access may be obtained either by unscrewing a plastic plug or by puncturing a septum of said T-tube with a needle. Other methods are also known.

It is known in the art to measure different parameters during dialysis or during a blood treatment in general. In particular, several methods are known for the detection of parameters relating to the access, such as access flow, or to access recirculation during a blood treatment.

For instance, U.S. Pat. No. 5,312,550 teaches to detect access recirculation of freshly dialyzed blood by infusing a marker in the extracorporeal circuit and by detecting presence of said marker in the blood to be treated.

Another document, EP900094, discloses a method for detecting access recirculation by infusion of saline into the dialysis liquid upstream the dialyzer and by detection of a corresponding echo downstream the dialyzer due to recirculation.

U.S. Pat. No. 5,685,989 teaches to detect access flow by using a reversed configuration of the bloodlines in an extracorporeal circuit. A marker is then infused in the venous line and a corresponding amount of said marker is then measured in the arterial line in order to calculate access flow. Of course other systems and methods are also known.

It is also known in the art to detect parameters relating to the central cardiovascular system, i.e. to the heart-lung system, in particular during a dialysis treatment.

Parameters of interest are the cardiac output, which is a measure of the capacity of the heart, and the central blood volume, which is a measure of the volume of blood in the heart, lung and central grand vessels. Notice that a proper monitoring of said parameters during dialysis may help in avoiding or in predicting dangerous situations of too low cardiac output or of excessive decrease of central blood volume. Methods for measuring the cardiac output and central blood volume related parameters are described in U.S. Pat. No. 5,453,576 and in U.S. Pat. No. 6,061,590. In these patents the detection of cardiac output/central blood volume parameters is obtained by injection of substance in blood circulating in an extracorporeal circuit and then by carrying out a detection of the injected fluid made by ultrasonic measurements on the blood side of the dialysis filter. The equipment that is used to make the ultrasonic measurements is quite expensive and needs use of means not present in a typical blood treatment apparatus.

Moreover the ultrasonic measurement method requires manual intervention by qualified attendants and is relatively difficult to be implemented with a high degree of automation. Thus there is a need for a different method and apparatus of measuring cardiac output, heart-lung volume or other central blood system related parameters. Ideally such a method and apparatus should use means already present in a blood treatment apparatus and should be suitable for calculating even other parameters in case of need or interest.

SUMMARY OF THE INVENTION

An object of the present invention is to provide an alternative means for measurement of a parameter relating to the heart-lung system of a mammal, particularly when a blood treatment apparatus is connected to the mammal.

Another object of the present invention is to provide a method of measuring the cardiac output of a heart in a mammal during blood treatment.

A further object of the present invention is to provide a method of measuring the central blood volume in a mammal.

Still another object of the present invention is to provide a method and an apparatus, which in case of need can be easily adapted for measuring the access flow during dialysis of a mammal.

At least one of these objects may be achieved with a method, apparatus and software program according to the present invention. According to a first aspect of the present invention a method, apparatus and software program are provided for determining a parameter relating to the heart-lung system, such as cardiac output or heart-lung volume of a mammal being connected to a blood treatment equipment comprising an extracorporeal blood circuit which is connected to a mammal, in which blood circuit a treatment unit having a blood inlet, a blood outlet, a treatment fluid inlet and a waste fluid outlet is arranged. The method comprises the steps of providing a change of a detectable substance in the blood circuit, measuring an integrated concentration of a corresponding the detectable change on the waste fluid outlet, and determining the parameter based on the measurement on the waste fluid outlet.

With such a method many of the problems with the prior techniques are avoided. One such problem is that prior techniques for solving this are more expensive.

According to an embodiment of the present invention, the step of providing a change includes the injection of a detectable substance upstream the blood treatment unit on the blood side.

Alternatively the substance is injected on the treatment liquid side upstream the treatment unit. The substance that is injected may be a substance that occurs naturally in the blood.

According to a further embodiment, the substance is injected during a short period of time so that to define a pulse perturbation. This avoids that the injected substance returns from the body before the injection has ended, thus avoiding that the different pulses are mixed.

According to another embodiment the pulse is provided by bypassing the dialyzer for a time period. This is a non-complicated way of providing a detectable pulse. In the case where a detectable substance is provided by insertion in the blood circuit one possibility is to have the substance inserted at the blood inlet. This provides a possibility of measuring the substance on the dialysis liquid side (or treatment liquid side) directly after the insertion of the detectable substance in the blood circuit and also a possibility of measuring the clearance if the injected amount is known.

Alternatively the substance may be injected on the blood outlet. This is preferable if the amount of injected substance is to be minimized, as no substance is lost in the dialyzer or other treatment unit. An advantage is also that there is no risk of mixing pulses during detection. A disadvantage with this is, however, that it is not possible to determine the clearance.

In conclusion, the detectable substance or other detectable change in a characteristic of the fluid in question, may be inserted at one of at least three different positions, namely upstream or downstream the treatment unit on the blood side, and upstream the treatment unit on the treatment liquid side.

Notice that even though in the above summary, for sake of clarity, reference has been made to a physical infusion of a substance, the principles of the invention are indeed based on the concept of creating a perturbation of a chemical or physical property (such as concentration, conductivity, an optical property, temperature and so on) in at least one of the above mentioned points, and then calculating the relevant heart-lung system parameter by means of a detection carried out on the spent treatment liquid side only.

By way of example, and in order to provide the cardiac output of the patient being connected to the extracorporeal circuit for instance of a dialysis equipment, the following method can be used according to a further embodiment of the invention.

The clearance for the dialysis filter is provided together with the flow rate on the dialysate side and the excess mass of the detectable substance in the pulse, the excess mass being the mass above the background level. In case the substance that is injected is not normally present in the blood the excess mass is equal to the mass. Then an integrated concentration change from a background level of the detectable substance on the dialysate output side is determined during a time interval when blood that has passed through the heart of the mammal passes the dialyzer. Finally, a cardiac output is calculated based on the integrated concentration change from the background level of the detectable substance on the dialysate side, the flow rate on the dialysate side, the clearance and the excess mass of the detectable substance in the pulse.

The described method of determining the cardiac output has advantages over the prior art methods in that it does not require as complicated equipment as the prior art methods. As an example it is possible to use the conductivity changes of the dialysis liquid when determining the cardiac output of the patients heart. As sensors for conductivity measurements often are in place on the dialysis liquid side in extracorporeal blood circuits for other reasons, it is not necessary to add any components in order to be able to perform the measurement of the cardiac output.

According to an embodiment of the present invention the cardiac output (CO) is calculated using the relationship:

$$CO = \frac{M \cdot K}{Q_d \cdot \int \Delta C_d dt}$$

where M is the excess mass, above a base level, of the detectable substance in the pulse, $Q_d$ is the flow rate on the dialysis side, K is the clearance and $\int \Delta C_d dt$ is the integrated concentration change on the dialysis side.

This is a relatively straightforward technique to calculate the cardiac output. It is of course possible to use other relationships to calculate the cardiac output without departing from the invention.

In the described embodiments the cardiac output was determined using a provided clearance. The clearance may be provided in a number of different ways. According to one embodiment of the present invention the clearance is provided from, e.g. data sheets for dialyzers.

According to another embodiment of the present invention the method comprise the step of providing the detectable substance by injecting the substance upstream the blood inlet. Further, a first and a second integrated concentration change from a background level is determined during a first and second pass of the detectable substance. Then, the clearance is determined from the first integrated concentration change, and the cardiac output is determined from the second integrated concentration change. The man skilled in the art would easily implement a clearance determination from the integrated concentration change. The clearance is a well-known term which is used to specify how efficient a dialyzer is. The clearance is specified at a certain blood flow rate and a certain dialysis fluid flow rate.

According to another embodiment, the present invention also comprises the steps of measuring the time between the first and the second concentration change, providing the volume of the blood in the extracorporeal blood circuit and the blood circuit within the mammal from the extracorporeal blood circuit to the heart, and determining the blood volume in the heart-lung system using the measured time, the provided blood volumes and the cardiac output.

This additional measurement is done in order to determine the blood volume in the heart-lung system. In order to get a good approximation of said blood volume it may be necessary to estimate the blood volume in the extracorporeal blood circuit and the veins leading from the extracorporeal blood circuit. Methods for determining the blood volume in the heart-lung system are known before but they are based on a different type of measurement of the cardiac output. Again, a major difference between the known techniques and the technique according to the present invention is that we measure the detectable substance on the dialysate or spent treatment liquid side.

As indicated above the method and system according to the present invention may comprise the step of measuring the clearance of the dialysis filter.

According to an embodiment of the present invention the detectable substance is urea. This is a non-toxic substance, which is present naturally in the blood.

According to an embodiment of the present invention and again referring by way of example to a dialysis treatment, the urea concentration is measured on the dialysis side by the steps of providing the urea in a reaction with a catalyst to form a second substance which affects the conductivity of the dialysis fluid, and measuring the resulting change in conductivity.

There are of course numerous different substances that might be used. Examples of substances are a salt, which may be injected on the blood side as a solution like hypertonic or hypotonic saline, and glucose, which may be injected as a solution in water.

According to a further embodiment of the present invention the concentration change may be measured by measuring the conductivity of the dialysis fluid.

It goes without saying that the above features may be combined in the same embodiment.

In the following preferred embodiments of the invention will be described with reference to the accompanying drawings.

SHORT DESCRIPTION OF THE ACCOMPANYING DRAWINGS

FIG. 1 displays how an extracorporeal blood circuit may be connected to a patient during performance of a method according to an embodiment of the present invention.

FIG. 2 displays a blood treatment equipment that may be used in a method according to an embodiment of the present invention.

DESCRIPTION OF PREFERRED EMBODIMENTS

Figure 3:
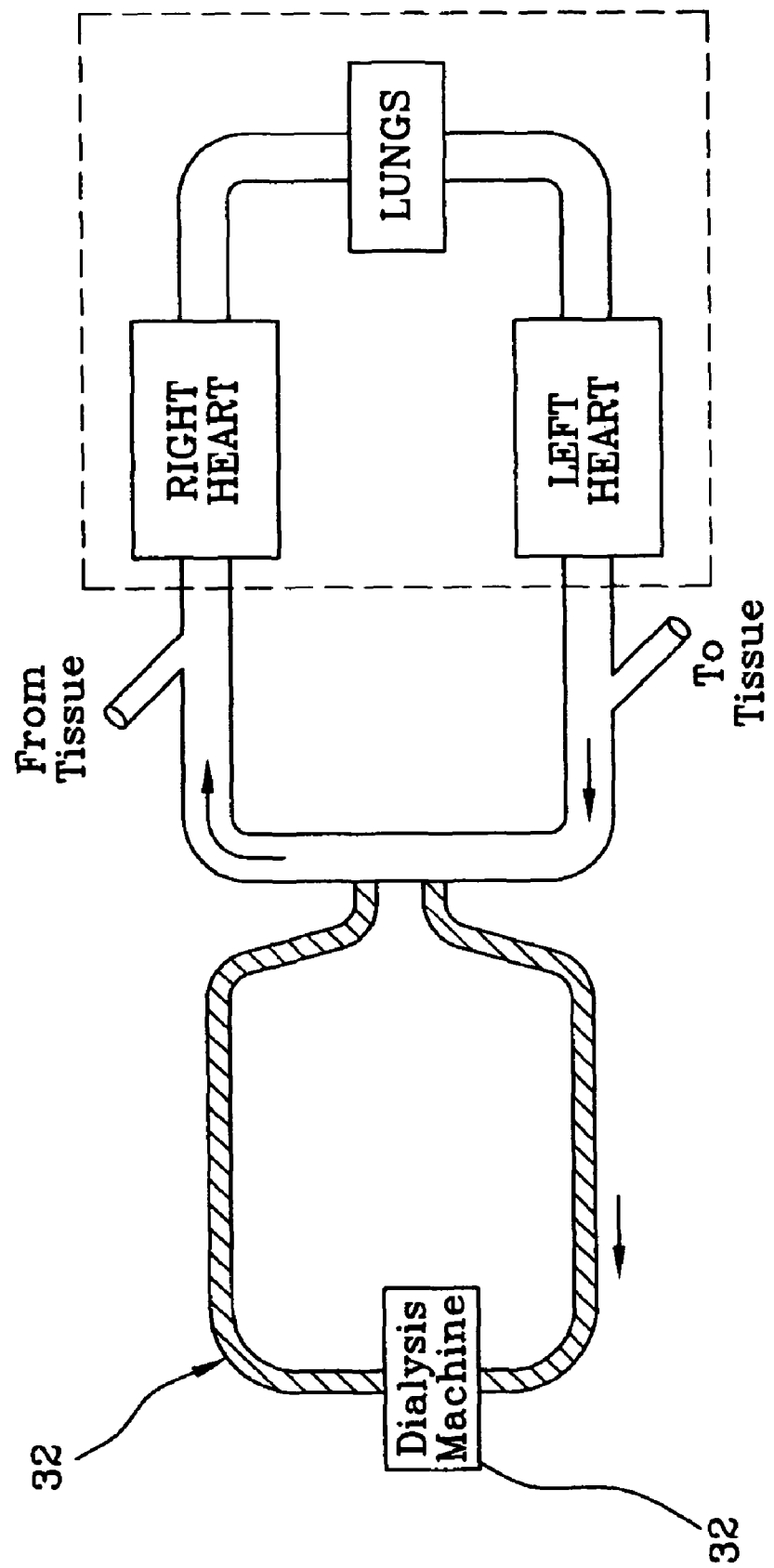
FIG. 3 is a schematic diagram over an extracorporeal blood circuit and a heart-lung system.

For the purpose of this description, an access site is a site in which a fluid in a tube can be accessed and removed from and/or returned to the tube. The tube may be a portion of a blood vessel of a mammal.

FIG. 1 discloses a forearm 1 of a human patient. The forearm comprises an artery 2, in this case the radial artery, and a vein 3, in this case the cephalic vein. Openings are surgically created in the artery 2 and the vein 3 and the openings are connected to form an area 4, in which the arterial blood flow is cross-circuited to the vein. Due to above connection, the blood flow through the artery and vein is increased and the vein forms a thickened area downstream of the connecting openings. After a few months the vein becomes thicker and may be punctured repeatedly. Normally, the thickened vein area is called fistula.

An arterial needle 5 is placed in the fistula, in the enlarged vein close to the connected openings and a venous needle 6 is placed downstream of the arterial needle, normally at least five centimeters downstream thereof.

The needles are connected to a tube system 7 shown in FIG. 2, forming an extracorporeal circuit comprising at least a blood pump 8. The blood pump propels blood from the blood vessel, through the arterial needle, the extracorporeal circuit, the venous needle and back into the blood vessel.

The extracorporeal blood circuit 7 shown in FIG. 2 further comprises an arterial clamp 9 and a venous clamp 10 for isolating the patient should an error or any emergency situation occur.

Downstream of pump 8 is a blood treatment unit, for instance a dialyzer 11, comprising a blood compartment 12 and a dialysis fluid compartment 13 separated by a semi permeable membrane 14. Further, downstream of the dialyzer, the circuit may include a drip chamber 15, separating air from the blood therein.

Blood passes from the arterial needle past the arterial clamp 9 to the blood pump 8. The blood pump drives the blood through the dialyzer 11 and further via the drip chamber 15 and past the venous clamp 10 back to the patient via the venous needle. The drip chamber may comprise air or air bubbles. The blood circuit may comprise further components such as pressure sensors etc.

The dialysis fluid compartment 13 of the dialyzer 11 is provided with dialysis fluid via a first pump 16, which obtains dialysis fluid from a source of pure water, normally RO-water, and one or several concentrates of ions, metering pumps 17 and 18 being shown for metering such concentrates.

An exchange of substances between the blood and the dialysis fluid takes place in the dialyzer through the semi permeable membrane 14. Notably, urea is passed from the blood, through the semi permeable membrane and to the dialysis fluid present at the other side of the membrane. The exchange may take place by diffusion under the influence of a concentration gradient, so called hemodialysis, and/or by convection due to a flow of liquid from the blood to the dialysis fluid, so called ultrafiltration, which is an important feature of hemodiafiltration or hemofiltration.

As mentioned above the present invention provides a method, and an apparatus for operating said method of measuring a parameter during a blood treatment when a mammal is connected to the dialyzer or other treatment unit.

FIG. 3 shows the heart/lung-system of a patient connected to the dialyzer as described in connection to FIG. 1.

An arterial needle 5 is placed in the fistula, in the enlarged vein close to the connected openings and a venous needle 6 is placed downstream of the arterial needle, normally at least five centimeters downstream thereof.

The needles are connected to a tube system 7 shown in FIG. 2, forming an extracorporeal circuit comprising a blood pump 8, such as a dialysis circuit. The blood pump propels blood from the blood vessel, through the arterial needle, the extracorporeal circuit, the venous needle and back into the blood vessel.

Mathematical Relationships

Next some relationships will be provided which are useful for the following description. Again, by way of non-limiting example, reference will be made to the case wherein a dialysis equipment is connected with the mammal.

When a bolus of detectable substance is inserted into the blood flow the concentration of said substance will rise above a base level. During insertion of the bolus into a biological fluid the flow of fluid will increase, but after a short while the flow is back to normal. If the concentration is measured at a point sufficiently far downstream of the insertion point, the fluid flow rate will increase immediately and then return to normal as soon as the insertion is completed. The increase in concentration will occur a certain time after the increase in fluid flow rate, so that these two changes will be separated in time.

If one injects a bolus of detectable fluid during a time $\Delta t1$ and detects a concentration change during a time $\Delta t2$ thereafter, not overlapping $\Delta t1$, the total mass $M_{tot}$ that passes through said point sufficiently downstream the insertion point during the time $\Delta t = \Delta t1 + \Delta t2$ will be as follows $$M_{tot} = \int_{\Delta t} Q \cdot c \, dt$$
$$= \int_{\Delta t1} Q \cdot c_{base} \, dt + \int_{\Delta t2} Q_{base} \cdot c \, dt$$
$$= \int_{\Delta t1} Q \cdot c_{base} \, dt + \int_{\Delta t2} Q_{base} \cdot c_{base} \, dt + \int_{\Delta t2} Q_{base} \cdot \Delta c \, dt$$

wherein the subscript "base" denotes the baseline for concentration and flow, $\Delta c$ denotes the concentration deviation from the baseline $c_{base}$. The first two integrals in the result correspond to the normal mass flow that would occur with the increased flow rate at the base line concentration, while the last integral equals the excess mass (caused by the change in concentration due to the bolus), which will be denoted by M. The concentration of the detectable substance in the dialysis fluid will be denoted $c_d$ downstream the dialyzer, and $c_i$ upstream the dialyzer. The concentration of the detectable substance on the blood side will be denoted $c_b$ upstream the dialyzer and $c_o$ downstream the dialyzer.

The amount of detectable substance, which is removed from the blood side in the dialyzer, equals the amount that has been provided into the dialysate liquid. This can be expressed as $$K[c_b - c_i] = Q_d[c_d - c_i] \quad (1)$$

with the notation described above, clearance denoted by K and $Q_d$ denoting the dialysate flow rate leaving the dialyzer. The concentration $c_o$ is calculated from $c_b$ and removed amount using the relation $$(Q_b - UF) \cdot (c_o - c_i) = (Q_b - K)(c_b - c_i) \quad (2)$$

Using equation (1) this can be written as $$(Q_b - UF) \cdot (c_o - c_i) = \frac{Q_b - K}{K} Q_d (c_d - c_i) \quad (3)$$

Now let us denote the total amount of substance in the bolus (with volume V) by $M_{tot}$. The excess amount M in the bolus (in addition to the concentration in the dialysate liquid) is then $M = M_{tot} - c_{ib} \cdot V$, where $c_{ib}$ is the base line concentration in the fresh dialysate. Similarly, the base line concentration in the dialysate outlet will be denoted by $c_{db}$ and in the blood inlet and outlet $c_{bb}$ and $c_{ob}$ respectively.

Depending on the site for bolus injection part of the excess amount M may be lost in the dialyzer and will not reach the patient. The excess amount that is provided to the patient will be denoted by M'.

Clearance Determination

Clearance determination or clearance knowledge is relevant in order to then implement heart-lung parameters detection according to the present invention, as it will become apparent in the following description.

Here below several modes for in vivo clearance determination are shown, other modes being known in the art and representing possible alternatives for clearance calculation. By way of non-limiting example, refer to EP1108438, EP0920877, EP0658352, and EP0547025, the specifications of which are herein incorporated by reference.

The clearance is a well-known term used to specify how efficient a dialyzer is. The clearance is specified at a certain blood flow rate and a certain dialysis fluid flow rate. Notice that as an alternative to in vivo clearance measurement, clearance values provided by technical data sheets for the specific treatment unit at specific conditions of blood flow rate and treatment liquid flow rate could be used.

According to a possible embodiment the clearance is measured by introducing a pulse of a detectable substance into the blood. More specifically, this is done by introducing a bolus in the form of a saline solution in the extracorporeal blood circuit upstream from the dialyzer through the valve at the reference numeral 21 or by suction into the blood line before pump 8. The introduced saline solution is of known concentration and amount.

The following relation is valid for the relationship between the concentration change in the blood and the concentration change in the dialysis fluid.

$$K \int \Delta c_b \, dt = Q_d \int \Delta c_d \, dt,$$

wherein $Q_d$ is the flow of fluid leaving the dialyzer on the dialysate side. Since the right hand side is known or can be measured, K may be determined if the first integral can be determined.

However, this can be done from the excess mass injected into the blood and using equation (1):

$$Q_b \int \Delta c_b \, dt = M_{tot} - c_{bb} \cdot V = M_{tot} - \left( c_{ib} + \frac{Q_d [c_{db} - c_{ib}]}{K} \right) \cdot V$$

This gives $$Q_b \cdot Q_d \int \Delta c_d \, dt = Q_b \cdot K \int \Delta c_b \, dt$$
$$= K[M_{tot} - c_{bb} \cdot V]$$
$$= K[M_{tot} - c_{ib} \cdot V] - Q_d [c_{db} - c_{ib}] \cdot V$$
$$= K \cdot M - Q_d [c_{db} - c_{ib}] \cdot V$$

and thus $$K = \frac{Q_d}{M} \left[ Q_b \int \Delta c_d \, dt + (c_{db} - c_{ib}) \cdot V \right]$$

To determine the clearance we will thus measure the concentration change $\Delta c_d$ on the dialysate side and integrate this during the whole pulse. We also need to determine the base line difference between the concentrations at the dialysate inlet and outlet, which can be done during steady state conditions before or after the introduction of the bolus. Furthermore we need to know the excess mass and volume of the bolus, and the blood and dialysate flow rates.

As an alternative the bolus may be injected into the dialysate flow upstream of the dialyzer. The calculations will then be different. The excess mass M in the bolus will give rise to a concentration change in the inlet dialysate according to $$M = M_{tot} - c_{ib} \cdot V = (Q_d - UF) \int \Delta c_i \, dt$$

According to equation (1) above we have a relation between all the concentration changes $K[\Delta c_b - \Delta c_i] = Q_d[\Delta c_d - \Delta c_i]$ But during the pulse in the dialysate there is no change in the blood concentration so that $\Delta c_b = 0$, and we can integrate to get $K \int \Delta c_i dt = Q_d [\int \Delta c_i dt - \int \Delta c_d dt]$ If we solve for K and insert the expression for M we get $$K = Q_d \left[ 1 - \frac{\int \Delta c_d dt}{M}(Q_d - UF) \right]$$

Again we thus measure the concentration change at the dialysate outlet and integrate. We also have to know the excess mass M, the dialysate flow rate $Q_d$ and the UF rate to calculate K.

Cardiac Output Measurement

According to an embodiment of the present invention the cardiac output is measured. This embodiment of the invention will be explained with reference to FIG. 2, FIG. 3, and FIG. 4. FIG. 3 is a schematic view over the heart lung system being connected to an extracorporeal circuit 31 with a dialysis machine 32. The extracorporeal circuit 31 with the dialysis machine 32 may be similar to that shown in FIG. 2. According to this embodiment of the present invention a bolus with a detectable substance is injected in the extracorporeal blood circuit upstream from the dialysis filter in the same way as was described above in relation to the clearance measurement. The total mass of the injected substance is denoted $M_{tot}$. The detectable substance passes the dialysis filter in which part of the detectable substance passes over to the dialysis fluid side. This passage gives rise to the first pulse of increased dialysate concentration shown in FIG. 4. On the dialysis fluid side the concentration change of the detectable substance is integrated over time. Similarly to the embodiment described above the clearance might be determined in case the amount of detectable substance is known.

Figure 4:
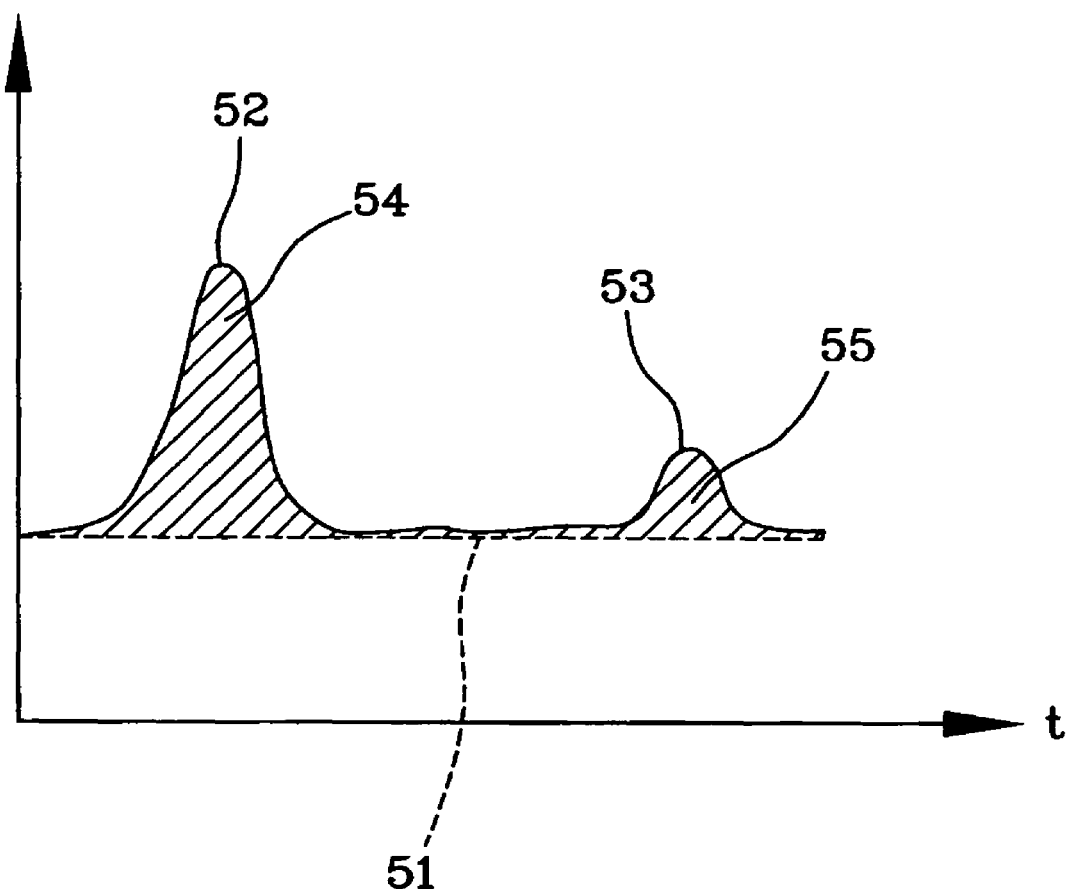
FIG. 4 is a diagram over concentration of the measurable substance as a function of time at the treatment liquid outlet of a blood treatment unit.

The injected substance gives rise to an excess mass in the blood above the base line concentration. After having passed the dialysis filter the blood with the detectable substance passes the access to the artery in the patient being connected to the extracorporeal blood circuit. The total excess amount that is left in the blood after the passage of the dialyzer is denoted M', which is equal to the excess mass minus the mass that passes over to the dialysis side during blood passage through the dialyzer. The blood with the detectable substance is then transported to the heart. As there is no blood taking any other path than to the heart all detectable substance is passing through the heart. Thus, the total amount of substance leaving the dialyzer is passing the heart but is diluted by the blood from the other parts of the body. The blood first passes the right heart side after which it is passed to the lungs and then through the left heart side. After the passage of the left heart side the blood is distributed within the body and some of the blood is returned to the access and into the extracorporeal blood circuit. The blood that enters the extracorporeal blood circuit is not diluted on its way from the heart and thus the detectable substance has the same concentration as in the heart. This makes it possible to determine the cardiac output as this is equal to the blood flow in the extracorporeal blood circuit times the factor of dilution of the blood when it flows from the extracorporeal blood circuit to the heart. The increased concentration in the blood coming from the heart will partly be transferred through the dialyzer and give rise to the second pulse of increased concentration on the dialysate side as shown in FIG. 4.

If the clearance is denoted K and the excess concentration of the detectable substance in the blood from the heart is denoted $\Delta C_b$ and the excess concentration of the detectable substance in the dialysate is denoted $\Delta C_d$ the following relation is valid $K \cdot \Delta C_b = Q_d \cdot \Delta C_d$, where $Q_d$ is the dialysate flow rate and $C_d$ is the dialysate concentration. The cardiac output may be determined from the relation:

$$CO = \frac{M' \cdot K}{Q_d \cdot \int_{II} \Delta C_d dt}.$$

In this relation the excess mass M' of the detectable substance, the clearance K and the dialysis liquid flow rate $Q_d$ are known, while the concentration change of the detectable substance in the dialysis liquid $\Delta C_d$ is measured. The integration of $\Delta C_d$ should be done over the length of the second pulse in FIG. 4, which is indicated with "II" under the integral sign.

The detectable substance may be any substance, such as saline or other detectable marker. The remaining excess mass M' which is passed over to the patient can be calculated as follows. From the total mass $M_{tot}$ is first subtracted the amount that corresponds to the base line blood concentration $c_{bb}$ in the injected volume V. This gives the excess mass in the blood after injection. From this amount is then subtracted the extra amount that passes over to the dialysate side directly during the first pulse in FIG. 4. We thus have $$M' = M_{tot} - c_{bb} \cdot V - Q_d \cdot \int_I \Delta C_d dt$$

But $c_{bb}$ can be derived from equation (1) so that $$M' = M_{tot} - \left[ \frac{Q_d(c_{db} - c_{ib})}{K} + c_{ib} \right] \cdot V - Q_d \cdot \int_I \Delta c_d dt$$

$$= M - \frac{Q_d(c_{db} - c_{ib})}{K} \cdot V - Q_d \cdot \int_I \Delta c_d dt$$

where M is the excess mass in the bolus, i.e. the mass corresponding to the excess concentration above the concentration of the dialysis fluid. The other parameters like the dialysate flow rate, the clearance, the bolus volume, the base line concentrations of the dialysate fluid inlet and outlet and the integral of the excess dialysate outlet concentration of the first pulse (indicated with I) are known or can be calculated. The inlet and outlet dialysate concentrations are often similar so that the second term can often be neglected.

As an alternative the bolus may be injected into the blood stream downstream of the dialyzer. There will then be no first passage of substance to the dialysate side, the first pulse shown in FIG. 4 will not be present, and it will therefore not be possible to determine clearance from the bolus injection. We will then have to rely on other means of determining clearance as have also been discussed above. The formula for determining cardiac output will remain unchanged, but the amount M' that is passed to the patient will be different since nothing is lost in the dialyzer. Using equation (3) we have $$M' = M_{tot} - c_{ob} \cdot V$$
$$= M - \frac{Q_b - K}{Q_b - UF} \cdot \frac{Q_d(c_{db} - c_{ib})}{K} \cdot V$$

Again all parameters needed are known or can be calculated.

Yet another alternative is to inject the bolus into the dialysis fluid upstream the dialyzer. This will again give rise to a first pulse on the dialysate outlet from which it is possible to determine clearance. It may however be necessary to delay the pulse on the blood side, e.g. by introducing an extra volume in either of the blood lines. The first and second pulses may otherwise be overlapping, and it will then not be possible to determine their respective integrals.

The excess mass passed to the patient may in this case be calculated by subtracting what is passed to the dialyzer from the excess mass in the bolus.

$$M' = M_{tot} - c_{ib} \cdot V - Q_d \cdot \int_I \Delta c_d dt$$
$$= M - Q_d \cdot \int_I \Delta c_d dt$$

Heart-Lung Volume

According to another embodiment of the present invention the blood volume in the heart lung-system is measured. According to this embodiment of the invention this is done by using the cardiac output (which could be already known or which could be measured as above disclosed) and by measuring the total time for the detectable substance to flow through the extracorporeal circuit, the blood vessels and the heart-lung system. Indeed, in this embodiment too a perturbation to a measurable blood characteristic is carried out, and a corresponding change on a corresponding characteristic in the spent treatment liquid is detected.

More in detail, the perturbation may be carried out on the blood side (either upstream or downstream the treatment unit) or on the treatment liquid side upstream the treatment unit. Such a perturbation comprises an infusion of a bolus of liquid such as a water solution of salt, or glucose, or other material. According a non-limiting embodiment, the infusion is of short duration as to create a pulse, which will shape corresponding perturbation(s) in the spent treatment liquid.

The volume in the heart-lung system is equal to the product of the cardiac output and the time for the blood to pass the heart-lung system. In order to obtain this time one has to subtract the time for the blood to flow through the extracorporeal circuit and through the blood vessels from the measured total time.

The time for the blood to flow through the extracorporeal circuit may easily be determined as this blood flow is well controlled and as the internal dimensions of the circuit are known.

Another possibility is to create a shortcut, so that the blood directed to the patient goes back to the extracorporeal circuit directly without passing the heart-lung system of the patient, and then make a new bolus injection and measure the time between the two pulses in this configuration. This will give an accurate determination of the time for the blood to flow through the extracorporeal circuit. The shortcut may be created just outside the patient, so that, without entering the patient, the blood directed to the patient is redirected to the blood line leading back from the patient to the equipment, or in the access of the patient by switching the blood lines so that blood is withdrawn from the patient at a point downstream and is returned to a point upstream, thus creating an artificial recirculation through the access of the patient.

Regarding the time for the blood to reach the heart from the access and vice versa (vessel time) these times can be estimated from the dimensions of the circuit and earlier measured blood flows. Since these times are generally fairly short it may however be sufficient to use a fix value in the range of 1-3 seconds as an estimate of this time. Alternatively this time can be calculated as a function of access flow (which by the way can be determined according to the method disclosed here below): a simple approximation being Vessel time (in seconds)=1/Access flow (in L/min).

As to the total time, if the perturbation is carried out on the blood upstream the treatment unit or on the treatment liquid upstream the treatment unit, then the total time is measured as the time between a first pulse of detectable material and the second pulse of detectable material measured in the spent treatment fluid. As the detectable material is measured at the dialysis liquid side of the dialysis filter there is a small delay from the time when the detectable material enters the dialysis filter and when it reaches the detector, but this delay will be the same for both pulses and can therefore be neglected.

The point in time when the pulse passes can be measured in the following way. A reference time is chosen some time before the pulse starts. Two integrals are then computed from the starting time through the duration of the pulse. The measured time from the reference time to the passage of the pulse is then determined as $$T_{measured} = \frac{\int t \cdot \Delta c_d dt}{\int \Delta c_d dt}$$

$\Delta C_d$ being the excess dialysate outlet concentration with respect to the base line concentration.

The time between the pulses is then calculated straightforwardly as the difference between the two measured times using the same reference time.

For the case when the bolus is injected into the blood stream at a point downstream of the dialyzer there will only be one pulse on the spent treatment liquid. The exact time of the bolus infusion may then be used as a value for the passage of the first pulse.

In FIG. 4 a diagram over the measured signal of the detectable substance downstream of the outlet of the dialysis filter on the dialysis side is shown as a function of time. The dotted line 51 corresponds to the background level of the signal. The first peak 52 of the solid line corresponds to the first passage of the dialysis filter of the detectable substance. The second peak 53 of the solid line corresponds to the second pass of the dialysis filter of the detectable substance.

Other Patient Parameters: Access Flow

As already anticipated the same means used for carrying out the necessary measurements and calculations needed for determining the heart-lung system parameters can be adopted for determining (in addition to or independently from the above parameters) access flow.

According to another embodiment of the invention the blood flow in the access can be determined by switching the flow direction of the blood and measuring the recirculation so created. In other words the blood circuit should be so configured as to withdraw fluid from a downstream point of the access and to return blood to an upstream point of the access. The flow rate in the access is measured by introducing a change, such as a pulse change of concentration of a detectable substance in the extracorporeal circuit. The excess amount M' of the substance that remains in the pulse when it enters the patient, whichever is the site used for injection, is calculated as above. Due to the reversed configuration of the blood circuit with respect to the access, all of M' will go into the access, and will be split up at the other needle where a fraction will go back to the extracorporeal circuit. The fraction of M' that goes back to the extracorporeal circuit and is measured on the dialysate side as a concentration change is in this case $$M' \cdot \frac{Q_b}{Q_b + Q_a - UF} = Q_b \cdot \frac{Q_d \cdot \int \Delta c_d dt}{K}$$

We can solve for $Q_a$ to get $$Q_a = \frac{K \cdot M'}{Q_d \cdot \int \Delta c_d dt} - (Q_b - UF)$$

Again the clearance K and the excess mass M' can be determined as described above and all the other quantities are known or can be measured.

Instead of calculating M' in the embodiment above there is another possibility. If we create a shortcut in the lines, excluding the patient as was described in the embodiment concerning heart-lung volume calculation above, we can measure how much of the bolus that remains in the line going to the patient if we in this configuration inject a second bolus. This can be looked upon as a calibration bolus.

The above methods are being carried out by means of a conventional blood treatment equipment such as the one of FIG. 2, which includes also a central processing unit able to run a software program which when executed by the processing unit allows the machine to perform the above disclosed methods.

Methods and apparatus for measuring parameters during an extracorporeal blood treatment, for instance during dialysis when an extracorporeal blood circuit is connected to the body of a mammal have been described.

The methods are all based on the initiation of a detectable perturbation, such as a pulse of detectable material, and the measurement of the detectable perturbation (material) on the spent treatment fluid (dialysis fluid) side of the treatment unit (dialysis filter).

The present invention is not limited to the described embodiments and a man skilled in the art may perform numerous modifications to the described embodiments without departing from the spirit and scope of the present invention, which is defined by the following claims.

The detectable perturbation can be a change in a chemical or physical property, such as infusion or withdrawal of a substance, which may for example be any one of the mentioned materials in any one of the described embodiments. Further, the detectable substances do not have to be any of the mentioned but can be any tissue-compatible detectable substance that can pass the dialysis filter or the sum of a number of ions as manifested by the electrical conductivity.

The invention claimed is:

1. A method for measuring a parameter relating to the heart-lung system of a mammal connected to blood treatment equipment, said equipment comprising an extracorporeal blood circuit connected to the mammal, said blood circuit including a blood treatment unit having a blood side, a blood inlet, a blood outlet, a treatment fluid side, a treatment fluid inlet, and a treatment fluid outlet, wherein said method comprises the steps of:
    providing a detectable perturbation to at least a measurable blood characteristic in the blood circuit, said detectable perturbation flowing through the heart-lung system and back to said blood circuit;
    measuring an integrated change of a corresponding characteristic on the treatment fluid outlet; and
    determining a parameter relating to the heart-lung system based on the measurement of said integrated change on the treatment fluid outlet.

2. A method according to claim 1, wherein the detectable perturbation to at least a measurable blood characteristic comprises a change in concentration of a detectable substance.

3. A method according to claim 1 or 2, wherein the detectable perturbation is carried out on the treatment fluid before the treatment fluid inlet, on the blood before the blood inlet, or on the blood after the blood outlet.

4. A method according the claim 2, wherein the change in concentration of a detectable substance comprises a pulse of detectable substance provided in the treatment fluid before the treatment fluid inlet.

5. A method according to claim 2, wherein the change in concentration of a detectable substance comprises a pulse of detectable substance provided by insertion of the detectable substance in the blood circuit.

6. A method according to claim 5, wherein the detectable substance is inserted before the blood inlet.

7. A method according to claim 5, wherein the detectable substance is inserted after the blood outlet.

8. A method according to claim 1, wherein said parameter relating to the heart-lung system comprises at least one selected in the group comprising:
    the cardiac output;
    a parameter proportional to the cardiac output;
    the heart-lung system volume; or
    a parameter proportional to the heart-lung system volume.

9. A method according to claim 8, further comprising the steps of:
    providing a clearance for the treatment unit, a flow rate on the treatment fluid side, and a mass of the detectable substance in said change,
    determining an integrated concentration change from a background level of the detectable substance on the treatment fluid side during a time interval determined by the time when blood, that has passed through the heart of the mammal, passes the treatment unit, and
    calculating the heart-lung system parameter based on the integrated concentration change from the background level of the detectable substance on the treatment fluid side, the flow rate on the treatment fluid side, the clearance, and the mass of the detectable substance in the change.

10. A method according to claim 9, wherein said change is a pulse.

11. A method according to claim 10 wherein the cardiac output CO is calculated using the relationship:

$$CO = \frac{M' \cdot K}{Q_d \cdot \int \Delta C_d dt}$$

where M' is the total excess mass of the detectable substance in the pulse, $Q_d$ is the flow rate on the treatment fluid side, K is the clearance and $\int \Delta C_d dt$ is the integrated concentration change on the treatment fluid side.

12. A method according to claim 11, wherein the change is carried out upstream the treatment unit, either in the blood circuit or in the treatment liquid, and corresponding first and second concentration pulses appear in the treatment liquid line downstream the treatment unit, said integration of $\Delta C_d$ being done over the length of the second pulse.

13. A method according to claim 12, wherein the change is carried out upstream the treatment unit, in the blood circuit, wherein $$M' = M_{tot} - \left[\frac{Q_d(c_{db} - c_{ib})}{K} + c_{ib}\right] \cdot V - Q_d \cdot \int_I \Delta c_d dt$$

$$= M - \frac{Q_d(c_{db} - c_{ib})}{K} \cdot V - Q_d \cdot \int_I \Delta c_d dt$$

M being the excess mass in the bolus corresponding to the excess concentration above the concentration of the treatment fluid, and wherein treatment fluid flow rate $Q_d$, the clearance K, the bolus volume V, base line concentrations of the treatment fluid inlet and outlet $C_{db}$ and $C_{jb}$, and the integral of the excess treatment fluid outlet concentration of the first pulse are known or calculated.

14. A method according to claim 12, wherein the change is carried out in the treatment liquid upstream the treatment unit, and the excess mass passed to the patient M' is calculated by subtracting what is passed to the treatment unit from the excess mass M in the bolus:

$$M' = M_{tot} - c_{ib} \cdot V - Q_d \cdot \int_I \Delta c_d dt$$

$$= M - Q_d \cdot \int_I \Delta c_d dt$$

M being the excess mass in the bolus corresponding to the excess concentration above the concentration of the treatment fluid, and wherein treatment fluid flow rate $Q_d$ and the integral of the excess treatment fluid outlet concentration of the first pulse are known or calculated.

15. A method according to claim 11, wherein the change is carried out in the blood circuit downstream the treatment unit, and wherein $$M' = M_{tot} - c_{ob} \cdot V$$

$$= M - \frac{Q_b - K}{Q_b - UF} \cdot \frac{Q_d(c_{db} - c_{ib})}{K} \cdot V$$

M being the excess mass in the bolus corresponding to the excess concentration above the concentration of the treatment fluid, and wherein treatment fluid flow rate $Q_d$, blood flow rate $Q_b$, ultrafiltration rate UF, clearance K, bolus volume V, base line concentrations of the treatment fluid inlet and outlet $C_{db}$ and $C_{jb}$ are known or calculated.

16. A method according to claim 8 or 10, further comprising the steps of providing the detectable change by injecting the substance either in the blood circuit upstream the blood inlet or in the treatment fluid side upstream the treatment unit, determining corresponding first and second concentration changes appearing in the treatment fluid line downstream the treatment unit determining the clearance from the first integrated concentration change, and determining the heart-lung parameter from the second integrated concentration change.

17. A method according to claim 8, further comprising the step of determining the heart-lung volume, or a parameter proportional to the heart-lung volume, as a product of the cardiac output and the time for the blood to pass the heart-lung system.

18. A method according to claim 17, further comprising the steps of:

measuring a total time for the blood to pass trough the extracorporeal circuit, from a vascular access site to the heart lung system, and out from the heart lung system back to the access site, providing the volume of the blood in the extracorporeal blood circuit and the blood circuit within the mammal from the extracorporeal blood circuit to the heart, and determining the blood volume in heart-lung system using the measured time, the provided blood volumes and the cardiac output.

19. A method according to claim 17, wherein said time for passing through the heart lung system is obtained by:

determining a total time for the blood to pass trough the extracorporeal circuit, from a vascular access site to the heart-lung system, and out from the heart lung system back to the access site, and subtracting, from said total time, the time for the blood to flow through the extracorporeal circuit, and the time to reach the heart-lung system from access site and the time for the blood to go back out from the heart-lung system to the access site.

20. A method according to claim 18 or 19, wherein the step of determining the total time is obtained as follows:

in case the detectable perturbation is a change in concentration of a detectable substance carried out either on the blood upstream the treatment unit or on the treatment liquid upstream the treatment unit, then the total time is calculated as time lag between a first and a second change in the concentration of a substance with respect to a background level in the spent treatment liquid line at the outlet of the treatment unit, in case the detectable perturbation is a change in concentration of a detectable substance carried out into the blood stream at a point downstream of the treatment unit, thereby giving only one change in the concentration of a substance with respect to a background level in the spent treatment liquid line at the outlet of the treatment unit, the total time is calculated as time lag between said change into the blood stream and the passage of said corresponding change in the spent treatment liquid.

21. A method according to claim 19, wherein the time for the blood to flow through the extracorporeal circuit is determined as a function of blood flow rate within the extracorporeal circuit and of the dimensions of the extracorporeal circuit.

22. A method according to claim 19, wherein the time for the blood to flow through the extracorporeal circuit is determined by:
- directing back to the extracorporeal circuit the blood which is returning to the patient, without passing through the heart-lung system of the patient,
- making a measurable change in at least a blood property in a section of said extracorporeal circuit, and
- measuring the time for said change to flow through the extracorporeal circuit.

23. A method according to claim 22, wherein the directing step is obtained by creating a shortcut just outside the patient, so that, without entering the patient, the blood directed to the patient is redirected to the blood line leading back from the patient to the equipment.

24. A method according to claim 22, wherein the directing step is obtained by switching the blood lines so that blood is withdrawn from the patient at a point downstream and is returned to a point upstream, thus creating an artificial recirculation through the access of the patient.

25. A method according to claim 19, wherein the time for the blood to reach the heart-lung from the access is estimated as a function of access flow.

26. A method according to claim 25, wherein the time, indicated as vessel time, for the blood to reach the heart-lung from the access is estimated as:

$$\text{Vessel time (in seconds)} = 1/\text{Access flow (in L/min)}.$$

27. A method according to claim 19, wherein the time for the blood to reach the heart-lung from the access is a fixed value in the range of 1-3 seconds.

28. Blood treatment equipment for implementing the method according to claim 1.

* * * * *

UNITED STATES PATENT AND TRADEMARK OFFICE
CERTIFICATE OF CORRECTION

| | | |
|---|---|---|
| PATENT NO. | : 7,815,852 B2 | Page 1 of 1 |
| APPLICATION NO. | : 10/990967 | |
| DATED | : October 19, 2010 | |
| INVENTOR(S) | : Jan Peter Sternby | |

It is certified that error appears in the above-identified patent and that said Letters Patent is hereby corrected as shown below:

In claim 18, column 16, line 22, "trough" should read --through--.

Signed and Sealed this
Twenty-fifth Day of January, 2011

David J. Kappos
*Director of the United States Patent and Trademark Office*